United States Patent [19]
Wood et al.

[11] Patent Number: 6,137,016
[45] Date of Patent: *Oct. 24, 2000

[54] PROCESS FOR THE PURIFICATION OF BUTANE-1,4-DIOL

[75] Inventors: Michael Anthony Wood, Middlesbrough; Paul Willett, Witton le Wear; Stephen William Colley, Redcar; Mohammad Shariff, Middlesbrough, all of United Kingdom

[73] Assignee: Kvaerner Process Technology Limited, London, United Kingdom

[*] Notice: This patent issued on a continued prosecution application filed under 37 CFR 1.53(d), and is subject to the twenty year patent term provisions of 35 U.S.C. 154(a)(2).

[21] Appl. No.: 09/155,441

[22] PCT Filed: Mar. 27, 1997

[86] PCT No.: PCT/GB97/00879

§ 371 Date: May 3, 1999

§ 102(e) Date: May 3, 1999

[87] PCT Pub. No.: WO97/36846

PCT Pub. Date: Oct. 9, 1997

[30] Foreign Application Priority Data

Mar. 29, 1996 [EP] European Pat. Off. .............. 96302259

[51] Int. Cl.⁷ .................................................. C07C 27/26
[52] U.S. Cl. ............................................................ 568/868
[58] Field of Search ............................................. 568/868

[56] References Cited

U.S. PATENT DOCUMENTS

| | | | |
|---|---|---|---|
| 2,768,214 | 10/1956 | McKinley | 568/868 |
| 4,383,895 | 5/1983 | Ernst et al. | 203/77 |
| 4,584,419 | 4/1986 | Sharif et al. | 568/864 |
| 4,751,334 | 6/1998 | Turner et al. | 568/864 |
| 4,795,824 | 1/1989 | Kippax et al. | 560/204 |
| 5,008,408 | 4/1991 | Fischer et al. | 549/429 |
| 5,397,439 | 3/1995 | Kandori | 568/868 |

FOREIGN PATENT DOCUMENTS

| | | |
|---|---|---|
| 58-167532 | 3/1983 | Japan . |
| 61-197534 | 1/1986 | Japan . |
| WO 88/00937 | 2/1988 | WIPO . |
| WO 90/08127 | 7/1990 | WIPO . |

OTHER PUBLICATIONS

International Search Report, PCT/GB 97/00879, Oct. 7, 1997 (3 pages).

*Primary Examiner*—Michael L. Shippen
*Attorney, Agent, or Firm*—Senniger, Powers, Leavitt & Roedel

[57] ABSTRACT

The invention provides a process for the purification of a butane-1,4-diol feed containing a minor amount of the cyclic acetal, 2-(4'-hydroxybutoxy)-tetrahydrofuran, which comprises hydrogenating the butane-1,4-diol feed in a hydrogenation zone in the presence of a minor amount of water and a hydrogenation catalyst, and recovering from the hydrogenation zone a butane-1,4-diol product that has a reduced 2-(4'-hydroxybutoxy)-tetrahydrofuran content compared with the butane-1,4-diol feed.

13 Claims, No Drawings

PROCESS FOR THE PURIFICATION OF BUTANE-1,4-DIOL

This invention relates to the production of butane-1,4-diol.

Butane-1,4-diol is used as a monomer in the production of plastics, such as polybutylene terephthalate. It is also used as an intermediate for the manufacture of γ-butyrolactone and of the important solvent, tetrahydrofuran.

One route to butane-1,4-diol involves reaction of acetylene with formaldehyde by the Reppe reaction to yield butyne-1,4-diol which is then hydrogenated to produce butane-1,4-diol.

Another process for production of butane-1,4-diol uses maleic anhydride as a starting material. This is esterified with an alkanol, usually a $C_1$ to $C_4$ alkanol such as methanol or ethanol, to yield the corresponding dialkyl maleate which is then subjected to hydrogenolysis to yield butane-1,4-diol and the alkanol which can be recycled to produce further dialkyl maleate. Processes and plant for the production of dialkyl maleates from maleic anhydride are described, for example, in U.S. application. Ser. No. 4795824 and in WO-A-90/08127. The hydrogenation of dialkyl maleates to yield butane-1,4-diol is discussed further in U.S. patent application Ser. No. 4584419, U.S. patent application Ser. No. 4751334, and WO-A-88/00937, the disclosures of all of which are herein incorporated by reference.

In the hydrogenolysis of a dialkyl maleate, such as dimethyl maleate or diethyl maleate, there may also be produced amounts of the valuable by-products, γ-butyrolactone and tetrahydrofuran. Since there is a ready market for these by-products, their co-production with butane-1,4-diol is not disadvantageous. In addition the hydrogenolysis product mixture will normally contain minor amounts of the corresponding dialkyl succinate, n-butanol, the corresponding dialkyl alkoxysuccinate, e.g. diethyl ethoxysuccinate, and water.

Another minor by-product has been identified as a cyclic acetal, i.e. 2-(4'-hydroxybutoxy)-tetrahydrofuran of the formula:

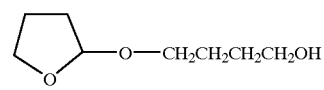

This is presumably formed by reaction of butane-1,4-diol with 4-hydroxybutyraldehyde which is a potential intermediate in the sequence of hydrogenolysis reactions or can be formed by dehydrogenation of butane-1,4-diol itself. The mechanisms for formation of all these products and by-products have not been fully elucidated. However, their production is consistent with the following reaction scheme:

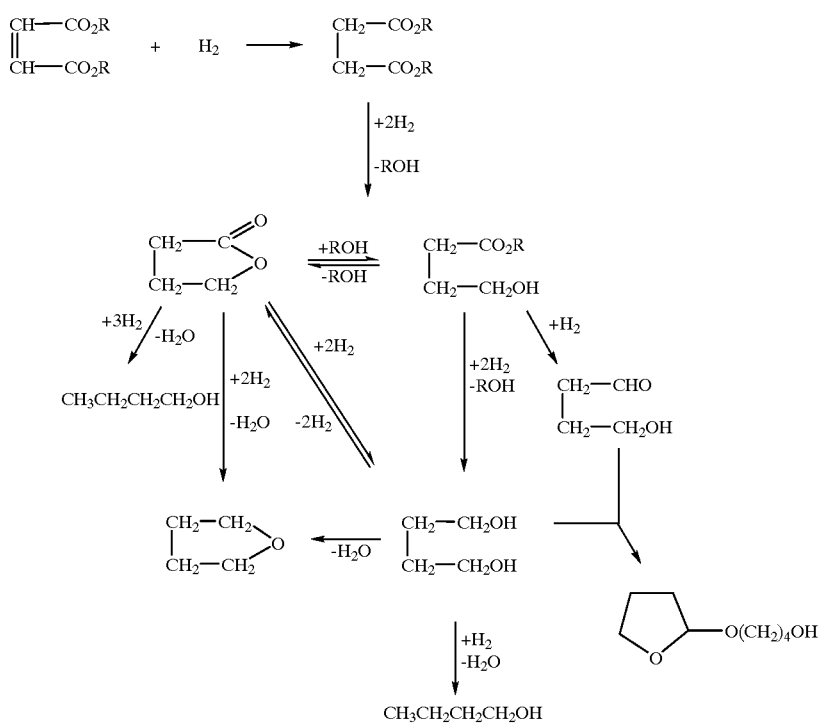

The cyclic acetal by-product, i.e. 2-(4'-hydroxybutoxy)-tetrahydrofuran, is troublesome because its boiling point lies very close to that of butane-1,4-diol and because it forms an azeotrope therewith. Hence it is difficult, if not impossible, to produce using conventional distillation techniques a butane-1,4-diol product which is essentially free from this cyclic acetal. Hence butane-1,4-diol produced by this hydrogenolysis route typically contains from about 0.15% by weight to about 0.20% by weight of the cyclic acetal with other impurities in total comprising no more than about 0.02% by weight. The presence of even minor traces of the cyclic acetal, 2-(4'-hydroxybutoxy)-tetrahydrofuran, in butane-1,4-diol is disadvantageous because it is a colour forming material and hence gives rise to colour formation in the butane-1,4-diol.

It has been proposed in U.S. patent application Ser. No. 4383895 to remove colour-forming materials present in crude butane-1,4-diol produced by hydrogenation of butyne-1,4-diol by subjecting the crude butane-1,4-diol to distillation under conditions wherein subjecting all of the water present in the crude butane-1,4-diol is first removed and then the butane-1,4-diol with reduced water content is further distilled to remove the colour-forming materials sufficiently to provide a product for use in the preparation of polyesters.

In JP-A-61/197534 there is taught a method of purifying crude butane-1,4-diol in which crude butane-1,4-diol containing at least one of the compounds, 2-(4'-hydroxy-butoxy)-tetrahydrofuran, 2-(4'-oxobutoxy)-tetrahydrofuran and 1,4-di-(2'-tetrahydrofuroxy)-butane, is hydrogenated in the presence of a hydrogenation catalyst, such as a supported platinum catalyst. The crude butane-1,4-diol can be prepared by acetoxylation of butadiene to yield diacetoxybutene which is then subjected to hydrogenation using a palladium or nickel catalyst and hydrolysis in the presence of a strongly acidic cation exchange resin. The specification goes on to describe how water and acetic acid are removed from the resulting hydrolysis product by distillation to yield the crude butane-1,4-diol which is the starting material for the method of purification. Since water has been removed by distillation, the crude starting material for the method product is substantially anhydrous. It is then described how aldehydes and acetals in the crude butane-1,4-diol are readily converted to compounds which can be separated easily from the butane-1,4-diol as a result of the hydrogenation method used for the purification method of this proposal. The document goes on to state that 2-(4'-hydroxy-butoxy)-tetrahydrofuran, 2-(4'-oxobutoxy)-tetrahydrofuran and 1,4-di-(2'-tetrahydrofuroxy)-butane are converted by hydrogenation to tetrahydrofuran, butane-1,4-diol, butanol, and ditetramethylene glycol, etc. The hydrogenated crude butane-1,4-diol is then subjected to distillation in two stages, a light boiling fraction containing water, tetrahydrofuran and butanol being recovered from the first distillation column. The second distillation column acts as the purifier, with butane-1,4-diol containing some light-boiling compounds being taken off from the top, butane-1,4-diol containing some heavy-boiling compounds being taken from the bottom, and the target purified butane-1,4-diol being taken from the side of the column.

It is accordingly an object of the present invention to provide an improved process for the purification of butane-1,4-diol which yields a butane-1,4-diol product stream that is essentially free from the cyclic acetal, i.e. 2-(4'-hydroxybutoxy)-tetrahydrofuran.

It is a further object of the present invention to provide an improved process for the production of butane-1,4-diol in which loss of potentially valuable butane-1,4-diol through formation of 2-(4'-hydroxybutoxy)-tetrahydrofuran as by-product is substantially obviated.

It is a still further object of the present invention to provide a process for the conversion of trace amounts of 2-(4'-hydroxybutoxy)-tetrahydrofuran present in butane-1,4-diol product streams to further butane-1,4-diol.

According to the present invention there is provided a process for the purification of a substantially anhydrous butane-1,4-diol feed containing a minor amount of the cyclic acetal, 2-(4'-hydroxybutoxy)-tetrahydrofuran, which comprises hydrogenating the butane-1,4-diol feed in a hydrogenation zone in the presence of a hydrogenation catalyst, and recovering from the hydrogenation zone a butane-1,4-diol product that has a reduced content of 2-(4'-hydroxybutoxy)-tetrahydrofuran, characterised in that hydrogenation is effected in the presence of from about 0.5% by weight up to about 5% by weight, based upon the weight of the butane-1,4-diol feed, of water. In such a process the added amount of water may correspond to a water:2-(4'-hydroxybutoxy)-tetrahydrofuran molar ratio of from about 20:1 to about 500:1.

Although the mechanism of the reaction has not been explored in detail, one plausible explanation is that, in the presence of the minor amount of water, the cyclic acetal is converted to a hemiacetal:

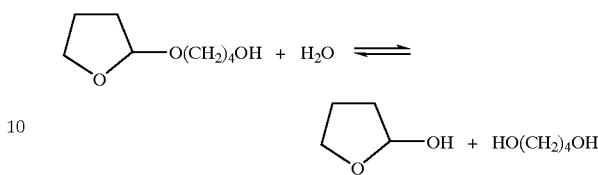

This hemiacetal is itself in equilibrium with the open chain compound, 4-hydroxybutyraldehyde:

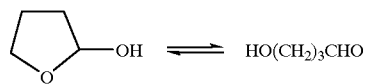

This can then be hydrogenated to butane-1,4-diol:

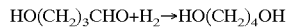

This is in contrast to the reactions involved in the purification method of JP-A-61/197534, in which the crude butane-1,4-diol used as starting material has already been distilled to remove acetic acid and water and so there is little or no possibility of the cyclic acetal, 2-(4'-hydroxy-butoxy)-tetrahydrofuran, being converted to the hemiacetal.

In a typical process according to the invention the butane-1,4-diol feed may contain from about 0.05% by weight up to about 1.0% by weight, typically about 0.1% by weight up to about 0.4% by weight, of 2-(4'-hydroxybutoxy)-tetrahydrofuran.

The hydrogenation catalyst is preferably a Group VIII metal-containing hydrogenation catalyst. Such Group VIII metal-containing catalysts typically contain from about 0.1% by weight up to about 2% by weight of a Group VIII metal or metals. As examples of Group VIII metals there can be mentioned nickel, palladium, platinum, rhodium, iridium, rhenium and the like, as well as mixtures of two or more thereof. The Group VIII metal or metals is or are deposited on an inert support, for example, graphite, alumina, silica-alumina, silica, zirconia, thoria, a diatomaceous earth or the like. A particularly preferred catalyst is a nickel catalyst. This can contain, for example, from about 10% by weight up to about 60% by weight or more of nickel. Another is a palladium-on-carbon catalyst, preferably containing from about 0.1% by weight up to about 4% by weight of palladium. A suitable nickel catalyst is that sold under the designation 86/4 by Kvaerner Process Technology Limited, of 30 Eastbourne Terrace, London W2 6LE.

Although the hydrogenation reaction can be conducted in the vapour phase, it is more conveniently carried out as a liquid chase reaction, using either a slurry of the catalyst or, more preferably, a fixed bed of catalyst. When operating with a fixed bed of catalyst the catalyst particles preferably have a particle size in the range of from about 0.5 mm to about 5 mm. The particles may be of any convenient shape, e.g. spheres, pellets, rings or saddles. When using a fixed bed of catalyst the reactor can be a shell-and-tube reactor, which can be operated substantially isothermally; however, it is preferably an adiabatic reactor. The use of an adiabatic reactor is advantageous since its capital cost is much lower than that of a shell-and-tube reactor and it is generally much easier to charge the reactor with the chosen catalyst.

The process of the invention requires the presence of a minor amount of water. Whilst a crude butane-1,4-diol stream may contain significant quantities of water, e.g. about 0.1% by weight to about 0.5% by weight, it is preferred to conduct the process of the invention as a polishing step, following one or more previous distillation steps for the separation of the butane-1,4-diol of other by-products, such as γ-butyrolactone, tetrahydrofuran, water, alkanol (e.g. methanol or ethanol), and n-butanol. Hence the butane-1,4-diol feed used in the process of the invention will normally be essentially anhydrous. Accordingly it will usually be necessary to add a minor amount of water thereto. Preferably sufficient water will be added to provide a molar ratio of water:2-(4'-hydroxybutoxy)-tetrahydrofuran of at least about 1:1 up to about 1000:1 or more, even more preferably from about 20:1 to about 500:1.

Hydrogenation is preferably conducted at an elevated temperature of, for example, from about 30° C. to about 170° C. Preferably the feed temperature to the hydrogenation zone is in the range of from about 50° C. to about 125° C. Similarly it is preferably conducted at an elevated pressure of, for example from about 50 psia (about 3.45 bar) up to about 2000 psia (about 137.90 bar), preferably from about 150 psia (about 10.34 bar) up to about 1000 psia (about 68.95 bar).

The butane-1,4-diol feed is preferably supplied to the hydrogenation zone at a liquid hourly space velocity in the range of from about 0.1 h$^{-1}$ to about 4.0 h$^{-1}$, preferably from about 0.5 h$^{-1}$ to about 1.5 h$^{-1}$. It can be admixed with an inert diluent prior to admission to the hydrogenation zone. Conveniently the diluent comprises butane-1,4-diol product recycled from the exit end from the hydrogenation zone. In this case the ratio of inert diluent to fresh feed preferably lies in the range of from about 1:1 to about 1000:1, for example from about 5:1 to about 100:1.

Following the hydrogenation step the butane-1,4-diol product, which is now essentially free from 2-(4'-hydroxybutoxy)-tetrahydrofuran, will normally be subjected to a final distillation step, preferably under an inert gas atmosphere, in order to remove any remaining trace of water and "heavies".

In this final distillation step there is a tendency, despite steps being taken to exclude oxygen, for the cyclic acetal to reform spontaneously, possibly due to the presence in the product of very small traces of 4-hydroxybutyraldehyde, 2-hydroxytetrahydrofuran and/or 2-ethoxytetrahydrofuran. However, the increase in cyclic acetal content is significantly less than that observed upon distillating the untreated butane-1,4-diol feed. Hence it has been observed that, if a butane-1,4-diol product recovered from the hydrogenation zone with a content of cyclic acetal, i.e. 2-(4'-hydroxybutoxy)-tetrahydrofuran, of about 0.03- by weight is heated under nitrogen at 160° C. for 5 hours, the cyclic acetal content rises to about 0.06% by eight.

The invention is further illustrated in the following Examples in which all percentages are by weight unless otherwise stated.

EXAMPLE 1

A continuously operable laboratory scale hydrogenation test rig was used for hydrogenation of a sample of a crude butane-1,4-diol from a commercial butane-1,4-diol production plant in which diethyl maleate is subjected to hydrogenolysis in the vapour phase using a reduced copper chromite catalyst. The rig was designed for liquid phase hydrogenation. The crude butane-1,4-diol contained 0.21% 2-(4'-hydroxybutoxy)-tetrahydrofuran and only a trace of water, typically about 0.02%. The sample was taken as a vapour stream from the distillation column designed to effect separation of unconverted diethyl succinate and γ-butyrolactone from the crude butane-1,4-diol (following removal by distillation of the volatile components, including water, ethanol, n-butanol and tetrahydrofuran from the crude reaction mixture from the hydrogenolysis zone).

The catalyst used in the Examples consisted of 1/16" (1.59 mm) nickel/alumina spheres of the type sold under the designation DRD 86/4 by Kvaerner Process Technology Limited of 30 Eastbourne Terrace, London. This contained 48.3% by weight of nickel, including 29.1% by weight of free nickel, and had a bulk density of 0.96 g/cm$^3$; it also contained only 0.08% by weight of particles that passed through a No. 20 sieve (U.S. Standard Sieve), (i.e. <850 mm), while 90% by weight of the particles passed through a No. 8 sieve (U.S. Standard Sieve), (i.e. <2.36 mm) and were retained on a No. 14 sieve (U.S. Standard Sieve), (i.e. >1.40 mm). 200 ml of the catalyst were charged to the reactor which was constructed from stainless steel, had an internal diameter of 1.065 inch (27.05 mm), and was fitted with a heating jacket which was designed to provide isothermal reaction conditions throughout the reactor. The catalyst charge was then activated by heating slowly to 100° C. under a flow of 600 NLPH of $N_2$. (The abbreviation NLPH denotes "normalised liters per hour", i.e. liters per hour measured at 0° C. and 1 bar). After raising the reactor temperature gradually to 140° C., 0.1% v/v $H_2$ was introduced into the gas flow for 1 hour. The $H_2$ concentration was then raised from 0.1% v/v to 1% v/v over a period of 1 hour while maintaining the reactor temperature at 140° C. Thereafter the $H_2$ concentration in the gas stream was slowly raised to 10%, still at 140° C., and then slowly to 100% v/v. The pressure was then raised to 900 psia (62.05 bar) and the reactor held at this pressure at 140° C.

Initially sufficient water was added to the crude butane-1,4-diol feed to raise the water content of the wet feed to 4%. (The stoichiometric amount required to hydrolyse the cyclic acetal was 0.05%). The results obtained at different operating temperatures, water contents, and liquid hourly space velocities (LHSV) are set out in Table I below. It will be observed from Table I that increasing the temperature by 10° C. from 110° C. to 120° C. results in an increase in the productivity of the catalyst by a factor of about 2 to about 3. Optimum results were obtained at a water content of about 2%.

TABLE I

| Run No. | 1 | 2 | 3 | 4 | 5 | 6 | 7 | 8 | 9 | 10 | 11 | 32 | 13 | 14 |
|---|---|---|---|---|---|---|---|---|---|---|---|---|---|---|
| Temp ° C. | 100 | 100 | 120 | 120 | 120 | 120 | 120 | 110 | 110 | 110 | 110 | 110 | 110 | 110 |
| Press, psia | 900 | 900 | 900 | 900 | 900 | 900 | 900 | 900 | 500 | 500 | 500 | 900 | 200 | 900 |
| Pressure, bar | 62.05 | 62.05 | 62.05 | 62.05 | 62.05 | 62.05 | 62.05 | 62.05 | 34.47 | 34.47 | 34.47 | 62.05 | 13.79 | 62.05 |
| Feedrate, | 100 | 200 | 200 | 300 | 100 | 540 | 770 | 220 | 200 | 200 | 200 | 200 | 200 | 200 |

TABLE I-continued

| Run No. | 1 | 2 | 3 | 4 | 5 | 6 | 7 | 8 | 9 | 10 | 11 | 32 | 13 | 14 |
|---|---|---|---|---|---|---|---|---|---|---|---|---|---|---|
| mls/hr | | | | | | | | | | | | | | |
| LWSV, $h^{-1}$ | 0.5 | 1 | 1 | 1.5 | 0.5 | 2.7 | 3.65 | 1.1 | 1 | 1 | 1 | 1 | 1 | 1 |
| Feed Composition | | | | | | Wt/Wt Percent | | | | | | | | |
| EtOH | 0.18 | 0.18 | 0.18 | 0.18 | 0.18 | 0.18 | 0.18 | 0.18 | 0.18 | 0.1B | 0.18 | 0.18 | 0.18 | 0.18 |
| THF | 0.008 | 0.008 | 0.008 | 0.008 | 0.008 | 0.008 | 0.008 | 0.008 | 0.008 | 0.008 | 0.008 | 0.008 | 0.008 | 0.008 |
| GBL | 0.606 | 0.606 | 0.606 | 0.606 | 0.606 | 0.606 | 0.606 | 0.606 | 0.606 | 0.606 | 0.606 | 0.606 | 0.606 | 0.606 |
| BDO | 94.403 | 94.403 | 94.403 | 94.403 | 94.403 | 94.403 | 94.403 | 94.403 | 94.403 | 97 | 97 | 97 | 96 | 94 |
| HVS | 0.612 | 0.612 | 0.612 | 0.612 | 0.612 | 0.612 | 0.612 | 0.612 | 0.612 | 1.015 | 0.015 | 0.015 | 1.015 | 1.015 |
| Acetal | 0.191 | 0.191 | 0.191 | 0.191 | 0.191 | 0.191 | 0.191 | 0.191 | 0.191 | 0.191 | 0.191 | 0.191 | 0.191 | 0.191 |
| $H_2O$ | 4 | 4 | 4 | 4 | 4 | 4 | 4 | 4 | 4 | 1 | 2 | 2 | 2 | 4 |
| Product | | | | | | Wt/Wt Percent | | | | | | | | |
| EtOH | 0.152 | 0.203 | 0.189 | 0.081 | 0.226 | 0.083 | 0.026 | 0.02 | 0.077 | 0.077 | 0.077 | 0.077 | 0.077 | 0.077 |
| THF | 0.027 | 0.017 | 0.06 | 0.045 | 0.12 | 0.037 | 0.05 | 0.03 | 0.039 | 0.039 | 0.039 | 0.039 | 0.039 | 0.039 |
| GBL | 0.588 | 0.607 | 0.613 | 0.582 | 0.595 | 0.59 | 0.57 | 0.57 | 0.574 | 0.606 | 0.606 | 0.606 | 0.606 | 0.606 |
| BDO | 94.56 | 94.41 | 94.314 | 94.672 | 94.421 | 94.61 | 94.65 | 94.76 | 94.685 | 96.4 | 95 | 96 | 96 | 94 |
| HVS | 0.594 | 0.676 | 0.782 | 0.579 | 0.611 | 0.59 | 0.594 | 0.56 | 0.513 | 1.76 | 2.188 | 1.199 | 1.134 | 1.231 |
| Acetal | 0.059 | 0.067 | 0.042 | 0.041 | 0.027 | 0.090 | 0.100 | 0.060 | 0.052 | 0.118 | 0.090 | 0.079 | 0.144 | 0.047 |
| $H_2O$ | 4 | 4 | 4 | 4 | 4 | 4 | 4 | 4 | 4 | 1 | 2 | 2 | 2 | 4 |

Notes to Table I:
THF = tetrahydrofuran
GBL = γ-butyrolactone
BDC = butane-1,4-diol
HVS = "heavies"
Acetal = 2-(4'-hydroxbutoxy)-tetrahydrofuran
LHSV = liquid hourly space velocity ($h^{-1}$)

EXAMPLE 2

A further experimental test rig, similar to that used in Example 1 but with provision for recycle of product butane-1,4-diol from the exit end of the hydrogenation zone for dilution of the crude butane-1,4-diol feed, was used in this example. It was charged with 250 ml (237.4 g) of the same catalyst as used in Example 1 which was activated in the same way. A series of 12 Runs was carried out. The analysis of the wet feed butane-1,4-diol, obtained by adding water to a crude butane-1,4-diol of the type used in Example 1, was as set out in Table II.

TABLE II

| | Runs 1–8 | Runs 9–12 |
|---|---|---|
| Water | 3.92 | 4.03 |
| Ethanol | 0.013 | 0.013 |
| Tetrahydrofuran | 0.003 | 0.003 |
| γ-butyrolactone | 0.444 | 0.443 |
| Butane-1,4-diol | 94.985 | 94.876 |
| Diethyl succinate | 0.013 | 0.013 |
| 2-(4'-hydroxybutoxy)-tetrahydrofuran | 0.175 | 0.175 |

In the first 4 Runs the effects of liquid recycle were investigated using an LHSV of 1.0 $h^{-1}$, a temperature of 110° C., a pressure of 900 psia (62.05 bar), and a hydrogen flow rate of 24 NLPH. In Run 1 the recycle rate was 2 kg $h^{-1}$, in Run 2 1 kg $h^{-1}$, in Run 3 0.6 kg $h^{-1}$, and in Run 4 0 kg $h^{-1}$. In Runs 5 to 12 the effects of hydrogen flow rate were investigated. Run 9 repeated the conditions of Run 8 after a weekend shutdown of the rig. Runs 10 to 12 used lower hydrogen flow rates. The results are summarised in Table III below.

TABLE III

| Run No | Temp, ° C. | $H_2$ Flow NLPH | LHSV $h^{-1}$ | Liquid Recycle kg/$h^{-1}$ | Feed $H_2O$ % wt | Feed Acetal % wt | Product Acetal % wt |
|---|---|---|---|---|---|---|---|
| 1 | 110 | 20 | 1.0 | 2 | 4.0 | 0.17 | 0.063 |
| 2 | 110 | 24 | 1.0 | 1.0 | 4.0 | 0.165 | 0.057 |
| 3 | 108 | 24 | 0.8 | 0.6 | 4.0 | 0.17 | 0.050 |
| 4 | 107 | 24 | 1.1 | 0 | 4.0 | 0.17 | 0.058 |
| 5 | 109 | 6 | 1.01 | 0 | 4.0 | 0.17 | 0.070 |
| 6 | 110 | 36 | 1.05 | 0 | 4.0 | 0.17 | 0.048 |
| 7 | 110 | 12 | 1.07 | 0 | 4.0 | 0.17 | 0.059 |
| 8 | 110 | 24 | 0.86 | 0 | 4.0 | 0.17 | 0.039 |
| 9 | 111 | 24 | 1.18 | 0 | 4.0 | 0.7 | 0.049 |
| 10 | 110 | 3 | 0.6 | 0 | 4.0 | 0.17 | 0.036 |
| 11 | 110 | 1.5 | 0.8 | 0 | 4.0 | 0.17 | 0.030 |
| 12 | 110 | 0.5 | 0.8 | 0 | 4.0 | 0.17 | 0.025 |

Notes
NLPH = normalised liters per hour
LHSV = liquid hourly space velocity
Acetal = 2-(4'-hydroxybutoxy)-tetrahydrofuran

EXAMPLE 3

A sample of the crude butane-1,4-diol used as feed in Example 2 and a sample of a butane-1,4-diol product after treatment by the procedure described in Example 2 were transferred to respective round-bottomed flasks blanketed with nitrogen. The temperature of the flasks was increased to 160° C., while allowing any water and "lights" to distill off. Samples were taken for analysis at intervals after the temperature reached 160° C. The results are set out in Table IV below.

TABLE IV

| Sample Time | Crude Acetal | Product |
| --- | --- | --- |
| 0 | 0.033 | 0.03 |
| 40 | 0.06 | 0.04 |
| 100 | 0.16 | 0.05 |
| 160 | 0.17 | 0.057 |
| 300 | 0.17 | 0.057 |

Note: Acetal = 2-(4'-hydroxybutoxy)-tetrahydrofuran

EXAMPLE 4

The general procedure of Example 1 is repeated using a 2% palladium on carbon catalyst, following the supplier's recommendations for activating the catalyst. At a temperature in the range of 100° to 125° C. using a hydrogen pressure of 200 psia (13.79 bar) to 900 psia (62.05 bar) similarly good results are obtained.

EXAMPLE 5

In this Example there was further investigated the effects of varying the amount of water added to a crude butane-1,4-diol of the type used in Example 1, using the apparatus of Example 2 and the same catalyst charge. The results obtained are set out in Table V.

Comparison of Runs 1, 3, and 9 of Table V shows that reducing the water content of the feed from 4.03% to 2.3% and then to 0.98% results in an increase of acetal in the product from 0.036% to 0.052% and to 0.08% respectively under otherwise similar conditions. The results set out in Table V also indicate that reducing the $H_2$ flow rate from 3.0 NLPH (normalised litres per hour, i.e. liters per hour at 0° C. and 1 ata [1.01 bar]) to 0.5 NLPH had a minimal effect upon acetal removal at the three water levels tested.

Runs 10 to 14 of Table V were intended to simulate the effect of an approximately 50% reduction in the activity of the catalyst by doubling the liquid hourly space velocity (LHSV) followed by an increase in catalyst temperature until the acetal content in the product was equivalent to that obtained at the lower LHSV. This resulted in the acetal content of the product increasing from 0.052% up to 0.099%. The catalyst temperature was increased in 5° C. increments whilst the other conditions were maintained substantially constant. These results indicate that a 10° C. increase in temperature would compensate for a 50% loss in catalyst activity.

At temperatures greater than 120° C. the acetal content started to increase; in addition the content of tetrahydrofuran increased as a result of dehydration of butane-1,4-diol.

Runs 15 to 17 of Table V showed that varying the pressure under otherwise substantially identical conditions affected the acetal content of the product. Run 17 produced essentially the same acetal content as Run 14, thus indicating that there was no significant loss of catalyst activity during the period of operation at the higher temperature.

In Runs 18 and 19 of Table V the activity of the catalyst was checked.

The γ-butyrolactone content of the feed was increased to 6% for Run 20 of Table V. This indicated that the presence of γ-butyrolactone does not appear to inhibit the removal of acetal from the purified butane-1,4-diol product.

TABLE V

| Run No. | Temp. (° C.) | Pressure (psig) [bar] | LHSV (hr$^{-1}$) | H$_2$ flow (NLPH) | Feed H$_2$O (%) | Acetal in product (wt %) | Acetal converted (%) |
| --- | --- | --- | --- | --- | --- | --- | --- |
| 1 | 110 | 885 [62.03] | 0.9 | 3.0 | 4.03 | 0.036 | — |
| 2 | 110 | 887 [62.17] | 0.77 | 0.4 | 4.03 | 0.025 | 79.75 |
| 3 | 110 | 908 [63.62] | 0.83 | 3.0 | 2.3 | 0.052 | 61.28 |
| 4 | 110 | 909 [63.69] | 0.89 | 1.4 | 2.3 | 0.047 | 67.32 |
| 5 | 110 | 897 [62.86] | 0.87 | 0.4 | 2.3 | 0.047 | 66.53 |
| 6 | 110 | 879 [61.62] | 0.95 | 0.5 | 2.3 | 0.054 | 64.77 |
| 7 | 110 | 917 [64.24] | 0.94 | 0.4 | 0.98 | 0.081 | 46.45 |
| 8 | 110 | 900 [63.07] | 0.90 | 1.4 | 0.98 | 0.083 | 42.55 |
| 9 | 111 | 908 [63.62] | 0.87 | 3.0 | 0.98 | 0.083 | 10.89 |
| 10 | 111 | 910 [63.76] | 1.73 | 3.0 | 1.99 | 0.099 | 64.40 |
| 11 | 115 | 900 [63.07] | 1.73 | 3.0 | 1.99 | 0.084 | 69.87 |
| 12 | 120 | 900 [63.07] | 1.68 | 3.0 | 1.99 | 0.049 | 81.94 |
| 13 | 125 | 900 [63.07] | 1.68 | 3.0 | 1.99 | 0.081 | 70.15 |
| 14 | 130 | 900 [63.07] | 1.69 | 3.0 | 1.99 | 0.072 | 73.53 |
| 15 | 130 | 700 [49.28] | 1.68 | 3.0 | 1.99 | 0.085 | 68.57 |
| 16 | 130 | 500 [35.49] | 1.68 | 3.0 | 1.99 | 0.032 | 88.21 |
| 17 | 130 | 900 [63.07] | 1.68 | 3.0 | 1.99 | 0.066 | 75.67 |
| 18 | 110 | 900 [63.07] | 1.05 | 24.0 | 1.99 | 0.046 | 72.87 |
| 19 | 110 | 900 [63.07] | 1.05 | 24.0 | 1.99 | 0.041 | 75.82 |
| 20 | 110 | 900 [63.07] | 1.05 | 24.0 | 1.99 | 0.029 | 82.90 |

We claim:

1. A process for the purification of a substantially anhydrous butane-1,4-diol feed containing a minor amount of the cyclic acetal, 2-(4'-hydroxybutoxy)-tetrahydrofuran, which comprises hydrogenating the butane-1,4-diol feed in a hydrogenation zone in the presence of a hydrogenation catalyst, and recovering from the hydrogenation zone a butane-1,4-diol product that has a reduced content of 2-(4'-hydroxybutoxy)-tetrahydrofuran, characterised in that hydrogenation is effected in the presence of from about 0.5% by weight up to about 5% by weight, based upon the weight of the butane-1,4-diol feed, of water.

2. The process according to claim 1 wherein the butane-1,4-diol feed contains from about 0.1% by weight up to about 0.4% by weight of 2-(4'-hydroxybutoxy)-tetrahydrofuran.

3. The process according to claim 1 wherein the butane-1,4-diol feed is a substantially anhydrous material obtained by the hydrogenolysis of a di-($C_1$ to $C_4$ alkyl) maleate followed by distillation of the hydrogenolysis reaction product to separate therefrom components including water and the alkanol formed by hydrogenolysis.

4. The process according to claim 1 wherein the hydrogenation step is conducted at a feed temperature in the range of from about 50° C. to about 125° C. and at a feed pressure in the range of from about 150 psia (about 10.34 bar) to about 1000 psia (about 68.95 bar).

5. The process according to claim 1 wherein the hydrogenation step is conducted using an amount of water corresponding to a water:2-(4'-hydroxybutoxy)-tetrahydrofuran molar ratio of from about 20:1 to about 500:1.

6. The process according to claim 1 wherein the hydrogenation catalyst is a Group VIII metal-containing catalyst.

7. The process according to claim 6 wherein the hydrogenation catalyst is a palladium-on-carbon catalyst containing from about 0.1% by weight up to about 4% by weight of palladium.

8. The process according to claim 7 wherein the hydrogenation catalyst is a nickel catalyst.

9. The process according to claim 1 wherein the butane-1,4-diol product from the hydrogenation step is distilled under an inert gas atmosphere to remove remaining traces of water therefrom.

10. The process according to claim 1 wherein the butane-1,4-diol feed is supplied to the hydrogenation zone at a rate corresponding to a liquid hourly space velocity of from about 0.5 $h^{-1}$ to about 4.0 $h^{-1}$.

11. The process according to claim 1 wherein the butane-1,4-diol feed is diluted with an inert diluent prior to entering the hydrogenation zone.

12. The process according to claim 11 wherein the inert diluent comprises butane-1,4-diol product recovered from the exit end of the hydrogenation zone.

13. The process according to claim 12 wherein the inert diluent:butane-1,4-diol feed ratio is in the range of from about 5:1 to about 100:1 by volume.

* * * * *